(12) United States Patent
Hägerkvist et al.

(10) Patent No.: US 7,875,616 B2
(45) Date of Patent: Jan. 25, 2011

(54) USE OF TYROSINE KINASE INHIBITOR TO TREAT DIABETES

(76) Inventors: Robert Per Hägerkvist, Höganäsgatan 7B, 75330 Uppsala (SE); Nils Richard Welsh, Luthagsesplanaden 14, 75225 Uppsala (SE)

( * ) Notice: Subject to any disclaimer, the term of this patent is extended or adjusted under 35 U.S.C. 154(b) by 240 days.

(21) Appl. No.: 10/556,984

(22) PCT Filed: May 26, 2004

(86) PCT No.: PCT/EP2004/005679

§ 371 (c)(1),
(2), (4) Date: Jun. 22, 2006

(87) PCT Pub. No.: WO2004/105763

PCT Pub. Date: Dec. 9, 2004

(65) Prior Publication Data

US 2007/0072932 A1 Mar. 29, 2007

(30) Foreign Application Priority Data

May 27, 2003 (GB) ................................. 0312086.2
Feb. 6, 2004 (GB) ................................. 0402682.9

(51) Int. Cl.
*A61K 31/497* (2006.01)
*A61K 31/505* (2006.01)

(52) U.S. Cl. ............................ 514/252.18; 514/252.14; 514/269; 514/272; 514/866

(58) Field of Classification Search ............ 514/252.18, 514/252.14, 269, 272, 866
See application file for complete search history.

(56) References Cited

U.S. PATENT DOCUMENTS 6,194,454 B1 * 2/2001 Dow ........................... 514/522

7,087,608 B2 * 8/2006 Atkins et al. ............ 514/252.18
2002/0022646 A1 2/2002 Avrutov et al.
2002/0035140 A1 3/2002 Moon et al.

FOREIGN PATENT DOCUMENTS

| EP | 564409 A1 * | 10/1993 |
|---|---|---|
| WO | WO 9903854 A1 * | 1/1999 |
| WO | 99/10325 | 3/1999 |
| WO | 01/64200 | 9/2001 |
| WO | WO 01/64200 | 9/2001 |
| WO | 02/055517 | 7/2002 |
| WO | 03/020698 | 3/2003 |
| WO | 03/097110 | 11/2003 |
| WO | WO 03/097110 | 11/2003 |
| WO | 2004/015082 | 2/2004 |
| WO | 2004/043408 | 5/2004 |

OTHER PUBLICATIONS

Veneri et al., "Imatinib and Regression of Type 2 Diabetes", The New England Journal of Medicine, vol. 352, No. 10, pp. 1049-1050 (Mar. 10, 2005).*
Lassila et al., "Imatinib attenuates diabetes-associated atherosclerosis," Arteriosclerosis, Thrombosis, and Vascular Biology, vol. 24(5), pp. 935-942, (May 2004).
Dumas J., "Protein kinase inhibitors: emerging pharmacophores 1997-2000," Expert Opinion on Therapeutic Patents, Ashley Publications, GB, vol. 11(3) pp. 405-429 (2001).

* cited by examiner

*Primary Examiner*—Kevin Weddington
(74) *Attorney, Agent, or Firm*—Ann R. Pokalsky, Esq.; Dilworth & Barrese, LLP

(57) ABSTRACT

The invention relates to the use of a c-Abl-, PDGF-R-, or c-kit- tyrosine kinase inhibitor, e.g. 4-(4-methylpiperazin-1-ylmethyl)-N-[4-methyl-3-(4-pyridin-3-yl)pyrimidin-2-ylamino)phenyl]-benzamide, or a pharmaceutically acceptable salt thereof for the manufacture of a medicament for the treatment of diabetes, e.g. type I diabetes, type II diabetes.

12 Claims, 2 Drawing Sheets

USE OF TYROSINE KINASE INHIBITOR TO TREAT DIABETES

The invention relates to the use of 4-(4-methylpiperazin-1-ylmethyl)-N-[4-methyl-3-4-pyridin-3-yl)pyrimidin-2-ylamino)phenyl]-benzamide, hereinafter referred to as "Compound I", or a pharmaceutically acceptable salt thereof for the manufacture of pharmaceutical compositions for the treatment of diabetes, e.g. type I diabetes or type II diabetes, to the use of Compound I or a pharmaceutically acceptable salt thereof in the treatment of diabetes, e.g. type I diabetes or type II diabetes, to a method of treating warm-blooded animals including mammals, especially humans, suffering from diabetes, e.g. type I diabetes or type II diabetes by administering to a said animal in need of such treatment a dose effective against said disease of Compound I or a pharmaceutically acceptable salt thereof.

LEGEND TO FIGURES

Figure 1:
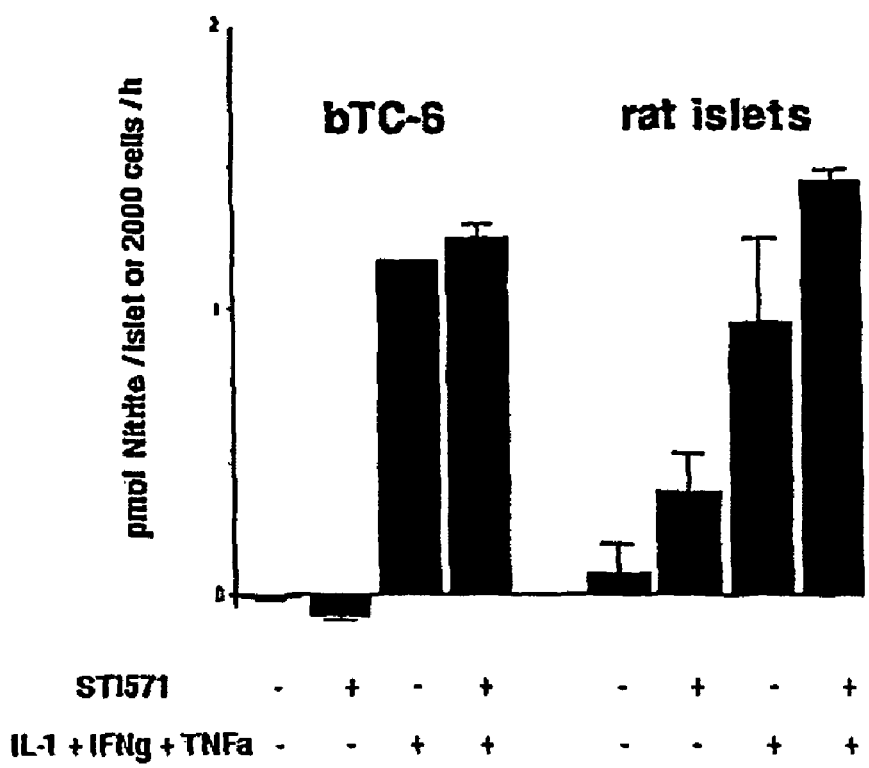

FIG. 1. Cytokine-induced NO production is not affected by 10 μM of Compound I, e.g. Salt I, in bTC-6 cells and isolated rat islets. Results are means± SEM for three independent observations.

Figure 2:
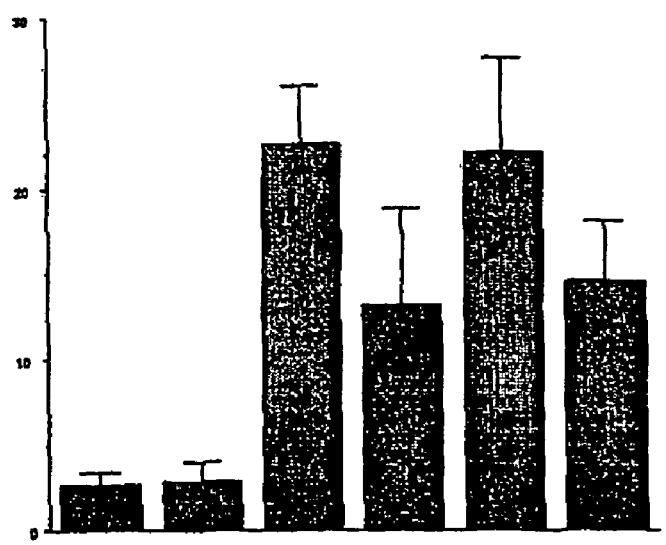

FIG. 2. Compound I, e.g. Salt I, partially protects human islet cells against nitric oxide. Results are means± SEM from three separate donors.

Figure 3:
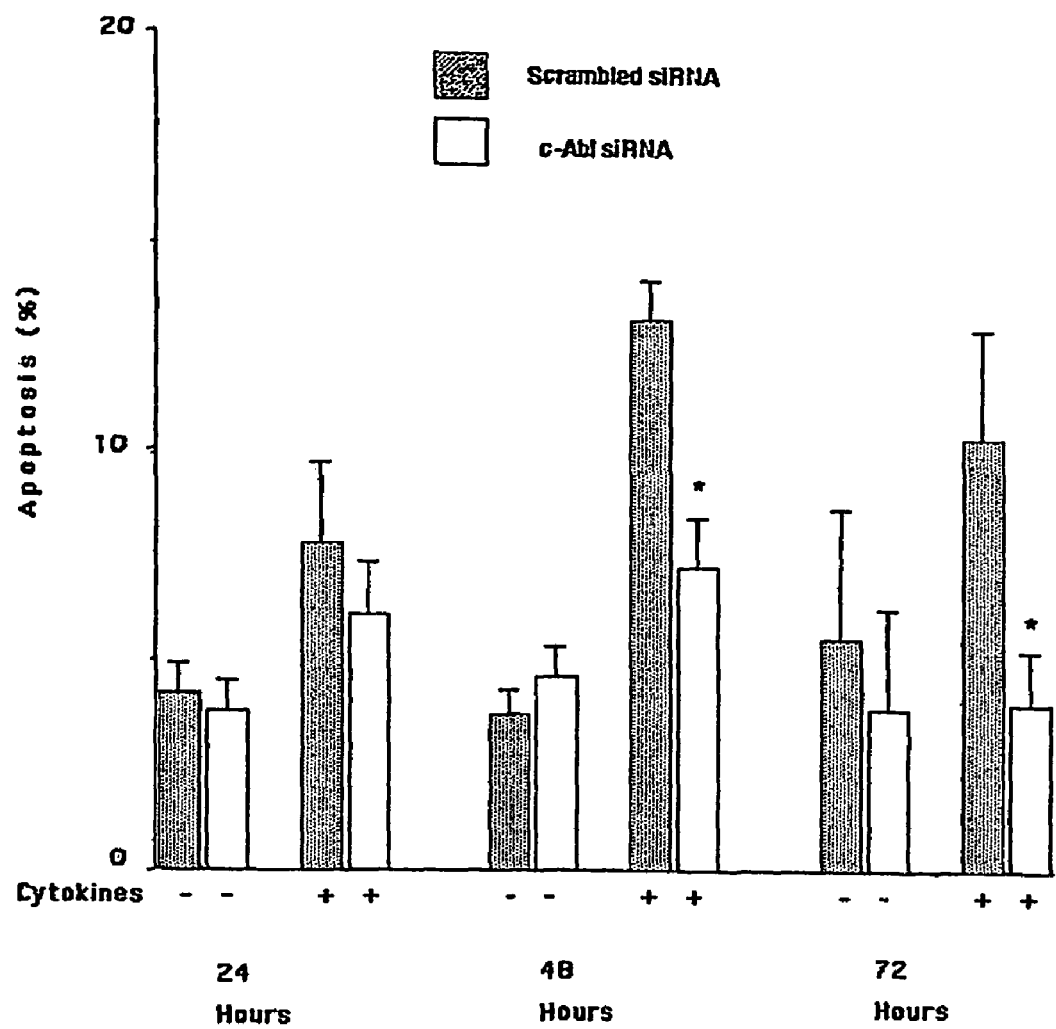

FIG. 3. Rates of apoptosis in bTC-6 cells treated with scrambled siRNA or c-Abl-specific siRNA. Cytokine treatment (IL-1β+IFN-γ+TNF-α) is initiated 24 h before analysis of cells. Apoptosis is quantified by flow cytometry. Results are means± SEM for 3-4 observations.

More than one million Americans have type 1 diabetes, also called insulin-dependent diabetes mellitus, abbreviated as IDDM, or juvenile diabetes. In type 1 diabetes, a person's pancreas produces little or no insulin, a hormone necessary to sustain life. Although the causes are not entirely known, type 1 diabetes is a multi-factorial autoimmune disease that results from the specific and progressive destruction of insulin producing beta-cells in the pancreas. It's one of the most costly, chronic diseases of childhood and one you never outgrow. While insulin allows a person to stay alive, it does not cure diabetes nor does it prevent its eventual and devastating effects: kidney failure, blindness, nerve damage, amputations, heart attack and stroke. To stay alive, those with type 1 diabetes must take multiple insulin injections daily or continually infuse insulin through a pump, and test their blood sugar by pricking their fingers for blood six or more times per day. While trying to balance insulin injections with their amount of food intake, people with type 1 diabetes must constantly be prepared for potential hypoglycemic, i.e. low blood sugar, and hyperglycemic, i.e. high blood sugar, reactions, which can be life threatening. Despite rigorous attention to maintaining a healthy diet, exercise regimen, and always injecting the proper amount of insulin, many other factors can adversely affect a person's blood-sugar control including: stress, hormonal changes, periods of growth, physical activity, medications, illness/infection, and fatigue. Even with insulin, type 1 diabetes usually results in a drastic reduction in quality of life and shortens the average life span by 15 years. Each year approximately 30,000 Americans are diagnosed with type 1 diabetes, over 13,000 of whom are children. That's 35 children each and every day.

Type 2 diabetes, also called non-insulin dependent diabetes mellitus, abbreviated as NIDDM, or adult diabetes, is usually associated with obesity, insulin resistance and a relative lack of insulin. Although this form of diabetes is in most cases non-insulin requiring, there are striking similarities between it and type 1 diabetes. For example, it is agreed today that there is an absolute lack of insulin producing beta-cells also in type 2 diabetes, and that this beta-cell deficiency is probably due to an increased rate of beta-cell death. Thus, pharmacological treatment that leads to protection against beta-cell death may be useful as a treatment of both type 1 and type 2 diabetes.

Surprisingly, it was found that a c-Abl-, PDGF-R-, c-kit-, or ARG- tyrosine kinase inhibitor or a pharmaceutically acceptable salt thereof e.g. Compound I or a pharmaceutically acceptable salt thereof, e.g. SALT I, is particularly useful for the treatment of diabetes, e.g. type I diabetes or type II diabetes. Unexpectedly, it was found that c-Abl-, PDGF-R-, c-kit-, or ARG-tyrosine kinase inhibitor or a pharmaceutically acceptable salt thereof, e.g. Compound I or a pharmaceutically acceptable salt thereof, e.g. SALT I, can be used to cure or to prevent diabetes, e.g. type I or type II diabetes.

Compound I is 4-(4-methylpiperazin-1-ylmethyl)-N-[4-methyl-3-(4-pyridin-3-yl)pyrimidin-2-ylamino)phenyl]-(benzamide) having the following formula

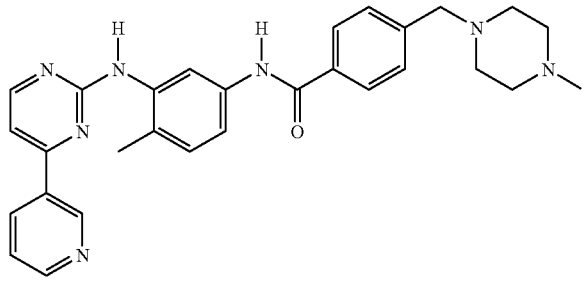

Compound I free base, its acceptable salts thereof and its preparation are disclosed in the European granted patent 0564409. Compound I free base corresponds to the active moiety.

The monomethanesulfonic acid addition salt of Compound I, hereinafter referred to as "Salt I", and a preferred crystal form thereof, e.g. the beta crystal form, are described in PCT patent application WO99/03854 published on Jan. 28, 1999.

The invention relates to the use of a c-Abl-, PDGF-R-, c-kit-, or ARG-tyrosine kinase inhibitor or a pharmaceutically acceptable salt thereof as a drug against diabetes, e.g. type 1 diabetes or type 2 diabetes. Most preferably, the invention relates in the use of Compound I or a pharmaceutically acceptable salt thereof, e.g. Salt I, as a drug against diabetes, e.g. type I diabetes or type II diabetes.

The c-Abl-, PDGF-R-, c-kit-, or ARG- tyrosine kinase inhibitors used according to the present invention are selected from the group comprising the following compounds: 4-(4-methylpiperazin-1-ylmethyl)-N-[4-methyl-3-(4-pyridin-3-yl)pyrimidin-2-ylamino)phenyl]-benzamide, herein after referred as Compound I, an inhibitor of PDGF-receptor isoforms, Bcr-Abl, and c-Kit, which stands out by high potency, and oral availability, Bis(1H-2-indolyl)-1-methanones another class of tyrosine kinase inhibitors which have been characterized as PDGF-R TK inhubitors as described in Mahboobi S et al., J. Med. Chem 2002, 45:1002-1018 and hereby incorporated by reference; the PDGF receptor kinase blocker AG1295 having the CAS Number 71897-07-9; AG1295/96 as described by Kovalenko M et al., Cancer Res. 1994 54:6106-6114 and Ludewig D et al., Cell Tissue Res. 2000, 299:97-103 and hereby incorporated by reference; CT52923 (4-(6,7-dimethoxy-4-quinolinyl)-N-(3,4-methylenedioxy-benzyl)-1-piperazinethiocarboxamide); RP-1776; GFB-111;

pyrrolo[3,4-c]-beta-carboline-diones, SU 102 (developed by SUGEN); AG1296 having the CAS Number 146535-11-7; RPR101511A developed by Aventis Pharma; CDP 860 and Zvegf3 developed by ZymoGenetics; CP 673451 and PD 170262 from Pfizer, KI 6783, having the CAS number 190726-45-5, an inhibitor of PDGF-R developed by Kirin Brewery, Japan; KN 1022 developed by Kyowa Hakko in Japan and Millenium Pharmaceuticals in US; AG 13736 developed by Pfizer; CHIR 258 developed by Chiron Corporation; MLN 518 from Millenium Pharmaceuticals and SU 11248 from SUGEN-Pfizer, Leflunomide; or pharmaceutically acceptable salts thereof.

CT52923 has been described by Matsuno K, et al., "Synthesis and structure activity relationships of PDGF receptor phosphorylation inhibitor-1." in 18th Symposium on Medicinal Chemistry; 1998 Nov. 25-27; Kyoto, Japan, the Pharmaceutical Society of Japan, Division of Medicinal Chemistry, Tokyo, Japan: Abstract 2-P-05.

RP-1776, a cyclic peptide, was isolated from the culture broth of Streptomyces sp. KY11784. It is described, e.g. by Toki S, Agatsuma T, et al., J. Antibiot. (Tokyo) 2001 May; 54(5):405-14.

GFB-111 is described, e.g. in Blaskovich Mass. et al., Nat. Biotechnol. 2000 October; 18(10):1065-70 and in Delarue F. et al, $91^{st}$ Annual meeting of the American Association for Cancer research, 41:458, 2000.

Pyrrolo[3,4-c]-beta-carboline-diones is described, e.g. by Teller S, Eur. J. Med. Chem 2000 April; 35(4):413-27. CDP 860 is a pegylated antibody fragment derived from the human anti-platelet derived growth factor beta receptor antibody.

CP 673451 targets the PDGF receptor.

PD 170262 or 2-[4-(2-diethlaminoethoxy)phenylamino]-8-methyl-6-(3-thienyl)pyrido[2,3-d]pyrimidin-7(8H)-one is a potent inhibitor of tyrosine kinase with selectivity for the platelet-derived growth factor tyrosine kinase. Synthesis and tyrosine kinase inhibitory activity of a series of 2-amino-8H-pyrido[2,3-d] pyrimidines is described, e.g. in Klutchko S. et al., $213^{th}$ American Chemical Society National meeting: abst MEDI 201(poster), 1997, USA.

KI 6783 or 4-(3,4-dimethoxyphenoxy)-6,7-dimethoxyquinoline is described, e.g. in Kubo K. et al, Bioorganic and Medicinal Chemistry Letters 7:2935-2940, 1997 and Yagi M. et al., Exp. Cell Research 234:285-92, 1997.

KN1022 or 6,7-dimethoxy-4-[4-(4-nitrophenyl)aminocarbonylpiperazin-1-yl]-quinazoline, which inhibits PDGFR phosphorylation, is described, e.g. in $217^{th}$ American Chemical Society National meeting abstr. MEDI 061, Part1, 1999, Japan.

AG 013736 or N-methyl-2-[3-[2-(2-pyridyl)vinyl]-1H-indazole-6-ylsulfanyl]-benzamide is disclosed, e.g. in Heller et al., Pharmacological activities of AG013736, a small molecule inhibitor of VEGF/PDGFR tyrosine kinases, $93^{rd}$ Annual meeting f the American association for Cancer research 43:1082, 2002, USA.

CHIR 258 is an orally active amino-benzimidazole quinoline growth factor kinase inhibitor which demonstrated a spectrum of inhibitory activity against receptor tyrosine kinases, e.g. from the PDGFR family. CHIR 258 is disclosed, e.g. in Steigerwalt R et al. and Lee S H et al. in $94^{th}$ Annual Meeting of the American Association for Cancer Research 753 (plus poster) abstr. 3783 and 934 (plus poster) abstr. R4702, respectively, 2003, USA.

SU11248 or 5-[3-fluoro-2-oxo-1,2-dihydroindol-(3Z)-ylidenemethyl]-2,4-dimethyl-1H-pyrrole-3-carboxylic acid (2-diethylaminoethyl)amine is multiple targeted kinase inhibitor with selectivity for, e.g. PDGFR. SU11248 is disclosed, e.g. in Xin L. et al., $93^{rd}$ Annual Meeting of the American Association for Cancer Research 43:1081 (plus poster), 2002, USA.

MLN 518 is a piperazinyl derivative of quinazoline of formula 4-[4-(N-para-iso-propoxyphenylcarbamoyl)-1-piperazinyl]-6-methoxy-7-(piperidinopropyloxy)-quinazoline that inhibits, e.g. PDGF R phosphorylation in binding assays, it is described, e.g. by Stone R M et al., Blood 102:65-66, 2003, Kelly L M et al., Cancer Cell 1: 421-23, 2002.

Leflunomide (SU 101) or 4-Isoxazolecarboxamide, 5-methyl-N-[4-(trifluoromethyl)phenyl] is a tyrosine kinase inhibitor.

SU11654 inhibits the tyrosine kinase activity of c-kit.

The structure of the active agents identified by code numbers, generic or trade names may be taken from the actual edition of the standard compendium "The Merck Index" or from databases, e.g. Patents International (e.g. IMS World Publications). The corresponding content thereof is hereby incorporated by reference.

The present invention further pertains to the use of 4-(4-methylpiperazin-1-ylmethyl)-N-[4-methyl-3-(4-pyridin-3-yl)pyrimidin-2-ylamino)phenyl]-benzamide, Bis(1H-2-indolyl)-1-methanones, AG1295, CT52923, RP-1776; GFB-111; pyrrolo[3,4-c]-beta-carboline-diones, SU 102, AG1296, RPR101511A, CDP 860, Zvegf3, CP 673451, PD 170262, KI 6783, KN 1022, AG 13736, CHIR 258, MLN 518, SU 11248, Leflunomide or a pharmaceutically acceptable salt thereof for the manufacture of a medicament for the treatment of diabetes, e.g type I diabetes or type II diabetes, preferably Compound I or a pharmaceutically acceptable salt thereof is used.

The present invention further pertains to the use of a c-Abl-, PDGF-R-, c-kit-, or ARG-tyrosine kinase inhibitor or a pharmaceutically acceptable salt thereof for the manufacture of a medicament to cure diabetes, e.g. type I diabetes or type II diabetes, preferably the c-Abl-, PDGF-R-, c-kit-, or ARG-tyrosine kinase inhibitor is selected from the group comprising 4-(4-methylpiperazin-1-ylmethyl)-N-[4-methyl-3-(4-pyridin-3-yl)pyrimidin-2-ylamino)phenyl]-benzamide, Bis(1H-2-indolyl)-1-methanones, AG1295, CT52923, RP-1776; GFB-111; pyrrolo[3,4-c]-beta-carboline-diones, SU 102, AG1296, RPR101511A, CDP 860, Zvegf3, CP 673451, PD 170262, KI 6783, KN 1022, AG 13736, CHIR 258, MLN 518, SU 11248, Leflunomide or a pharmaceutically acceptable salt thereof, preferably 4-(4-methylpiperazin-1-ylmethyl)-N-[4-methyl-3-(4-pyridin-3-yl)pyrimidin-2-ylamino)phenyl]-benzamide.

In the present description, the term "treatment" includes both prophylactic or preventive treatment as well as curative or disease suppressive treatment, including treatment of patients at risk of diabetes as well as ill patients. This term further includes the treatment for the delay of progression of the disease.

By "suppress and/or reverse diabetes" the applicant means that the diabetes condition is not longer present in the patient or that the disease is less severe than it was before or without the treatment.

The term "cure" as used herein means that the treatment leads to remission of diabetes or of ongoing episodes of diabetes.

The term "prophylactic" or "prevent" mean the prevention of the onset or recurrence of diabetes.

The term "delay of progression" as used herein means that the administration of the active compound to patients being in a pre-stage or in an early phase of diabetes prevent the disease to evolve further or slow down the evolution of the disease in comparison to the evolution of the disease without administration of the active compound.

The pharmaceutical compositions according to the present invention can be prepared in a manner known per se and are those suitable for enteral, such as oral or rectal, and parenteral administration to warm-blooded animals, including man, comprising a therapeutically effective amount of at least one pharmacologically active ingredient, alone or in combination with one or more pharmaceutically acceptable carries, especially suitable for enteral or parenteral application. The preferred route of administration of the dosage forms of the present invention is orally.

Hence, the invention also relates to a method of treating a warm-blooded animal having diabetes, e.g. type I diabetes or type II diabetes, comprising administering to said animal in need for such a treatment Compound I or a pharmaceutically acceptable salt thereof in a quantity which is therapeutically effective against.

The invention relates to a method of administering to a human subject suffering from diabetes, e.g. type I diabetes or type II diabetes, preferably type I diabetes, an acid addition salt of Compound I and preferably Salt I, the monomethanesulfonate salt of 4-(4-methylpiperazin-1-ylmethyl)-N-[4-methyl-3-(4-pyridin-3-yl)pyrimidin-2-ylamino)phenyl]-benzamide.

The person skilled in the pertinent art is fully enabled to select relevant test models to prove the beneficial effects mentioned herein on diabetes, e.g. type I diabetes or type II diabetes. The pharmacological activity of such a compound may, for example, be demonstrated by means of the Examples described below, by in vitro tests and in vivo tests or in suitable clinical studies. Suitable clinical studies are, for example, open label non-randomized, dose escalation studies in patients having diabetes, e.g. type I diabetes or type II diabetes. The efficacy of the treatment is determined in these studies, e.g., by evaluation of the disease every 4 weeks, with the control achieved on placebo.

The effective dosage of Compound I may vary depending on the particular compound or pharmaceutical composition employed, on the mode of administration, the type of the diabetes, e.g. type I or type II, being treated or its severity. The dosage regimen is selected in accordance with a variety of further factors including the renal and hepatic function of the patient. A physician, clinician or veterinarian of ordinary skill can readily determine and prescribe the effective amount of compounds required to prevent, counter or arrest the progress of the condition.

Depending on age, individual condition, mode of administration, and the clinical picture in question, effective doses, for example daily doses of Compound I or a pharmaceutically acceptable salt thereof corresponding to 100 to 1000 mg of the free base as active moiety, especially 800 mg, are administered to warm-blooded animals of about 70 kg body weight, Preferably, the warm-blooded animal is a human. For patients with an inadequate response to daily doses, dose escalation can be safely considered and patients may be treated as long as they benefit from treatment and in the absence of limiting toxicities.

The invention relates also to a method for administering to a human subject suffering from diabetes, e.g. type I or type II diabetes, Compound I or a pharmaceutically acceptable salt thereof, which comprises administering a pharmaceutically effective amount of Compound I or a pharmaceutically acceptable salt thereof to the human subject once daily for a period exceeding 3 months. The invention relates especially to such method wherein a daily dose of 400 to 800 mg preferably 800 mg, of Compound I is administered to an adult The invention further provides a medicament package comprising of a-c-Abl-, PDGF-R-, c-kit-, or ARG-tyrosine kinase inhibitor or a pharmaceutically acceptable salt thereof, e.g. Compound I, or pharmaceutically acceptable salts thereof, e.g. Salt I, together with printed instructions for administration to patients having diabetes, e.g. type I diabetes, type II diabetes.

EXAMPLE 1

Does Compound I, e.g. Salt I, Protect Against Beta-Cell Death and Diabetes?

In the following example, by β-TC6 cells refer as beta-TC6 cells.

Insulin-dependent (Type 1) diabetes mellitus (IDDM) is a multi-factorial autoimmune disease that results from the specific and progressive destruction of insulin producing β-cells. Dysfunction and damage of β-cells is thought to arise from a direct contact with islet-infiltrating cells (macrophages, $CD4^+$ or $CD8^+$ (NK)T-cells) and/or exposure to cytotoxic mediators produced by these cells, such as proinflammatory cytolines (IL-1, TNF-α, IFN-γ), free radicals, Fas ligand, TRAIL and perforin. Autoimmunity directed against beta-cells might be initiated by environmental factors such as beta-cell toxins, nutritional components, stress, metabolic overload, virus, . . . etc. It is likely that the beta-cell, by converting external death signal to internal apoptotic events, participates actively in its own destruction in type 1 diabetes. Pro-inflammatory cytokines, particularly the combination of IL-1 and IFN-γ, induce beta-cell apoptosis and necrosis. Thus, it is conceivable that these cytokines not only modulate the activity of islet infiltrating immune cells, but also exert direct noxious effects on the beta-cell in the pathogenesis of type 1 diabetes. It appears that stimulation of beta-cells with IL-1 leads to multiple signaling events including activation of protein kinases (PKC, p38, JNK, ERK, MSK1), lipases (PLC, PLD, sphingomyelinase), cyclooxygenase and transcription factors (NF-κB, ATF-2, c-jun, Elk-1, CREB, cEBP-β, IRF-1, STAT-1). These events are followed by induction of inducible nitric oxide synthase (iNOS) and stress-related proteins such as hsp70, heme oxygenase, Mn-SOD, ICE and others. Unfortunately, it is not clear which alterations in gene expression that are essential for beta-cell death in type 1 diabetes. Predominantly apoptosis occurs in a beta-cell line in response to UV-light or inhibition of DNA repair. This is preceded by p53 tumor suppressor protein induction, generation of reactive oxygen species, PARP inhibition, S- and $G_2$-cell cycle arrest and a decrease in the mitochondrial membrane potential. Cytokines, which promote mainly necrosis, and only to a lesser extent apoptosis, activated essentially the same signaling steps as inhibition of DNA repair or UV-light. From these in vitro experiments, it is clear that the beta-cell mode of death may vary depending on the death signal, but also that similar signaling pathways may be utilized to achieve different forms of beta-cell death.

C-Abl is a ubiquitously expressed protein tyrosine kinase with the approximate molecular weight of 145 kDa. Under physiological conditions, c-Abl has been shown to participate in the control of cytoskeletal functions, such as migration and cell structure, and cell cycle progression However, when cells are exposed to different forms of stress, c-Abl becomes highly activated, which leads to cell cycle arrest and apoptosis.

In summary, extensive studies in non-beta-cells have demonstrated that c-Abl promotes apoptosis in response to various types of stress. The putative role of c-Abl in insulin producing cells has not been elucidated. Thus, it is unclear whether this protein plays any role in beta-cell death and the decision between apoptosis and necrosis.

Significance to type 1 diabetes. Although the pathogenesis of type 1 diabetes appears very complex, it is possible that the intracellular pathways leading to beta-cell death converge at some particular point. Hypothetically, this could give us, employing only one approach, the possibility to block a multitude of death signals, thereby achieving beta-cell survival.

The tyrosine kinase c-Abl might be a significant mediator of beta-cell death. C-Abl is expressed in bTC-6 cells and in isolated rat islets, and inhibition of c-Abl activity, either using the pharmacological agent COMPOUND I or by knocking out c-Abl expression with the RNAi technique, resulted in protection against beta-cell death induced by proinflammatory cytokines or by nitric oxide donors. C-Abl does not act by promoting nitric oxide production, since inhibition of c-Abl did not counteract cytokine-induced nitric oxide production.

In view of these data, c-Abl acts a sensor of stress and external death signals and that c-Abl activation might lead to phosphorylation and activation of the JNK and p38 MAP kinases, inactivation of NF-κB and PI3K, the mitochondrial release of pro-apoptotic factors and filly beta-cell death. Compound I is capable of blocking different death signals, thereby achieving beta-cell survival and protection against diabetes.

Results: To establish whether Compound I, e.g. Salt I, interferes with or whether c-Abl participates in the signaling cascade that leads to beta-cell death, isolated rat islets are exposed to the slow releasing nitric -oxide donor DETA/NO (0.5 mM), or to the combination of IL-1β (25 U/ml)+IFN-γ (1000 U/ml)+TNF-α (1000 U/ml) for 24 h In both cases, islets are cultured with or without 10 μM of Compound I, e.g. Salt I, throughout the incubation period. Following the incubation period, islets are vital stained with propidium iodide+ bisbenzimide and photographed in a fluorescence microscope. Apoptotic (white condensed or fragmented nuclei) and necrotic (red or pink non-fragmented nuclei) are counted and expressed as percentage of total cell number. Salt I, e.g. Compound I, by itself does not affect islet cell viability. DETA/NO induces necrosis in 10% of the islet cells and the combination of cytokines approximately 40% necrosis. Interestingly, cell death induced by the NO donor is clearly counteracted by Compound I, e.g. Salt I, (Table 1). Also cytokine-induced islet cell necrosis is partially decreased by the c-Abl inhibitor. The frequencies of apoptotic cells are below 10% in all groups (results not shown).

TABLE 1

Compound I, e.g. Salt I, protects against NO- and cytokine induced islet cell death.

| Treatment | Without Compound I | With 10 μM Compound I |
| --- | --- | --- |
| Control | 1.4 ± 0.3 | 3.2 ± 0.9 |
| DETA/NO | 9.3 ± 1.2 | 4.9 ± 1.2* |
| IL-1 + IFN-γ + TNF-α | 41.6 ± 5.5 | 32.8 ± 3.2* |

Results are means ± SEM from three separate observations.

Levels of nitrite from cells incubated with the combination of cytokines given above for 24 hours, with or without 1 or 10 μM of Compound I, e.g. Salt I, are determined. Cytokine-induced nitric oxide production is not inhibited by Compound I, e.g. Salt I (FIG. 1). On the contrary, the nitric oxide production in the presence of Salt I is higher, possibly be due to the higher viability of the Salt I-exposed cells, 35% more nitrite released from cytokine plus Compound I exposed cells as compared to cytokines alone.

It is tested whether Compound I protects against the diabetogenic drug streptozotocin in vitro. At 0.4 mM streptozotocin, the protection is highly, significant, whereas at 0.75 mM streptozotocin, Compound I protects only weakly (Table 2). At 0.6 mM streptozotocin, the protective effect of Compound I is intermediate.

TABLE 2

Compound I, e.g. Salt I, protects against streptozotocin-induced islet cell death. Compound I (10 μM) is added 24 hours before streptozotocin. Islets are harvested and photographed six hours after addition of streptozotocin. Necrotic (red or pink non-fragmented nuclei) are counted and expressed as percentage of total cell number.

| Treatment | Without Compound I | With 10 μM Compound I |
| --- | --- | --- |
| Control | 0.9 ± 0.2 | 0.5 ± 0.2 |
| 0.4 mM streptozotocin | 86.3 ± 0.3 | 7.3 ± 2.4*** |
| 0.6 mM streptozotocin | 85.3 ± 5.5 | 41.3 ± 6.2** |
| 0.75 mM streptozotocin | 91 ± 3.5 | 75.3 ± 5.2* |

Results are percentage necrotic cells expressed as means ± SEM from three separate observations.
*,  and * denote p < 0.001, 0.01 and 0.05 using Students paired t-test.

To investigate whether Compound I, e.g. Salt I, regulates cell death also in human islet cells, human islets are incubated for 24 h with our without Compound I, e.g. Salt I, (10 μM), DETA/NO (2 mM) and Brefeldin A (10 μM. As observed with the rat islets, also human islets are partially protected against toxic levels of NO (FIG. 2). Thus, Salt I partially counteracts Brefeldin B-induced islet cell death (ER stress).

To investigate whether c-Abl regulates and/or whether Compound I, e.g. Salt I, also protects against streptozotocin-induced diabetes in vivo, the following procedure is used: Male NMRI mice, weighing about 25 g are purchased from Taconic M&B, Sollentuna, Sweden. The animals have free access to tap water and pelleted food throughout the study. The bedding material is changed weekly. Weight and blood glucose are determined using the Pen Sensor (MediSense, Waltham, Mass., USA) prior to the experiment. The animals are gavaged with 200 microliter Compound I, e.g. Salt I, dissolved in 0.9% NaCl 200 mg/kg body weight on three consecutive days (day—1, 0, 1). On day 0 mice are injected with 120 or 160 mg/kg bodyweight of streptozotozin (Sigma-Aldrich Co. St. Louis, Mo., USA) in the tail vein. Streptozotocin is dissolved in 0.9% NaCl just prior to injection. Weight and blood glucose are determined on day 0, 1, 2, 3, 5, 7, 9 on blood samples collected from the tail. On day 9 the animals are sacrificed by cervical dislocation. All animal experimentation is approved by the local Animal Ethics Committee (Tierp, Sweden).

Compound I treatment protects completely against the 120 mg/kg streptozotocin injection (Table 4). In addition, Compound I, e.g. Salt I, protects partially against the higher streptozotocin dose (160 mg/kg) (Table 3).

TABLE 3

Effect of Compound I, e.g. Salt I, on diabetes in mice induced by 160 mg/kg streptozotocin NMRI mice are fed 200 mg/kg Compound I by gavage once daily on day −1, 0 and 1. On day 0 the mice are injected with 160 mg/kg streptozotocin intravenously and the blood glucose is determined on the days given in the Figure.

| Day | Saline | Compound I | STZ | STZ + Compound I |
| --- | --- | --- | --- | --- |
| −2 | 8.6 ± 0.6 | 7.5 ± 0.7 | 8.2 ± 0.9 | 7.9 ± 0.4 |
| 0 | 7.4 ± 0.3 | 7.5 ± 0.6 | 8.5 ± 0.5 | 6.8 ± 0.4* |
| 1 | 7.6 ± 0.3 | 8.5 ± 0.8 | 10.3 ± 0.7 | 8.0 ± 0.3** |
| 2 | 8.5 ± 0.3 | 9.0 ± 0.5 | 20.2 ± 1.6 | 11.7 ± 0.7*** |

TABLE 3-continued

Effect of Compound I, e.g. Salt I, on diabetes in mice induced by 160 mg/kg streptozotocin NMRI mice are fed 200 mg/kg Compound I by gavage once daily on day −1, 0 and 1. On day 0 the mice are injected with 160 mg/kg streptozotocin intravenously and the blood glucose is determined on the days given in the Figure.

| Day | Saline | Compound I | STZ | STZ + Compound I |
| --- | --- | --- | --- | --- |
| 3 | 8.5 ± 0.4 | 9.1 ± 0.4 | 20.7 ± 0.5 | 13.5 ± 1.3*** |
| 5 | 7.6 ± 0.2 | 8.5 ± 0.6 | 21 ± 1.3 | 14.4 ± 1.4** |
| 7 | 7.7 ± 0.3 | 8.5 ± 0.5 | 25.6 ± 0.9 | 18.1 ± 2.1** |
| 9 | 8.7 ± 0.2 | 9.0 ± 0.4 | 27.2 ± 0.4 | 20.0 ± 2.4** |

*,  and * denote $p < 0.05$, 0.01 and 0.001 vs STZ using Student's t-test.
The number of observations is 5 (Saline and Compound I) and 10 (STZ and STZ + Compound I).

TABLE 4

Effect of Compound I on diabetes in mice induced by 120 mg/kg streptozotocin. NMRI mice are fed 200 mg/kg Compound I by gavage once daily on day −1, 0 and 1. On day 0 the mice are injected with 120 mg/kg streptozotocin intravenously and the blood glucose is determined on the days given in the Figure.

| Day | STZ | STZ + Compound I |
| --- | --- | --- |
| 0 | 8.9 ± 0.4 | 7.8 ± 0.3 |
| 1 | 9.9 ± 0.2 | 7.4 ± 0.3*** |
| 2 | 9.5 ± 0.5 | 7.4 ± 0.4* |
| 3 | 10.0 ± 0.8 | 8.2 ± 0.9 |
| 5 | 12.7 ± 1.5 | 9.0 ± 0.9* |
| 7 | 12.6 ± 1.2 | 8.8 ± 0.6* |

*and***denote $p < 0.05$ and 0.001, respectively, when comparing vs corresponding STZ group (Student's t-test). The number of observations is 10.

Research Design and Methods:

1. To identify additional death signals and stress factors that promote death of human beta-cells through Compound I inhibited pathways. Human islet cells are treated with 10 μM of Salt I, e.g. Compound I, and islet cell death determined in response to the following cytotoxic agents: hydrogen peroxide (150 μM; oxidative stress), staurosporin (200 nM, PKC-inhibition), FCCP (5 μM; uncoupling and mitochondrial membrane permeability transition), Brefeldin A (10 μM, ER stress), thapsigargin (200 nM, ER stress and increased $Ca^{2+}$) and doxorubicin (2 μM, DNA damage). Cell death is visualized by vital staining with propidium iodide and bisbenzimide followed by fluorescence microscopy. Islets in duplicate groups of 10 are used. This procedure allows quantification of both apoptosis and necrosis in intact islets. The vital staining technique is combined with the XTT assay (a simplified version of the MTT assay), which provides us with a simple and rapid screening assay of islet viability.

2. To study whether Compound I affects the development of diabetes in type 1 diabetes animal models. As described above, Compound I, e.g. Salt I, protects against a single dose streptozotocin injection. To extend this observation, the role of c-Abl in the development of diabetes in the multi-streptozotocin treated c57KSJ/black mouse model is evaluated. The daily Compound I treatments (200 mg/kg Compound I in 200 μl 0.9% NaCl) is started one day before the first streptozotocin treatment (daily low-dose 40 mg/kg injections for 5 days) and continue for ten days or two weeks when there is manifest diabetes. The treatment is evaluated by daily measurements of blood glucose values. After ten days or two weeks, the mice are sacrificed and the pancreas are removed and fixated for immunohistochemical and morphometric analysis. Islet inflammation and beta-cell mass is scored.

The importance of c-Abl in recurrence of disease in the non-obese diabetic mouse, abbreviated NOD mouse, is studied. A similar protocol is used as given above. However, in this case the Compound I treatment is given to diabetic female NOD mice. One day after the first Compound I administration by gavage, 300 islets isolated from young NOD mice are transplanted under the kidney capsule. After seven days glucose values are determined and the mice are sacrificed. At this time point most of transplanted beta-cells have been destroyed by the activated immune cells and any putative effect of Compound I on beta-cell survival is be detectable. The transplants are recovered and fixated for analysis.

Thirdly, the effect of Compound I is studied on the natural course of diabetes in NOD mice. Female NOD mice at the age of 4-5 weeks, when there is no or very little insulitis, receive Alzet mini-osmotic pumps subcutaneously that release 0.25 μ, per hour for four weeks of concentrated Compound I or vehicle alone. After the four weeks the mice are sacrificed and the pancreas is removed and fixated for immunohistochemical and morphometric analysis. The degree of insulitis and beta-cell mass is scored.

In view of the possibility that pharmacological inhibition of c-Abl might be problematic, a genetic approach is attempted. For this purpose, islets are isolated from c57/KSJ black and NOD mice and disperse islet cells by trypsin treatment The islet cells are transduced with recombinant adenoviral vector at 5 MOI that directs transcription of a c-Abl specific siRNA molecule. As control is used an adenoviral vector that encodes a scrambled siRNA sequence. The cells are then allowed to reaggregate for 5 days in vitro before implantation under the kidney kapsule of syngenic mice. The mice are treated and analyzed as given above.

It may be that adenoviral vector are unsuitable for in vivo purposes considering their inherent toxicity and immunogenicity. An AAV vector is constructed that expresses the same anti c-Abl siRNA construct Approximately 30% of islet beta-cells are transduced by AAV when dispersed in vitro (results not shown). This is considerably lower than the transduction efficiency obtained with adenoviral vectors, but is sufficiently high to allow evaluation of c-Abl in beta-cell destruction in vivo.

Methods and Facilities

Human islets. Human islets are cultured free floating at standard culture conditions (5.6 mM glucose in RPMI1640+ 10% FCS).

Flow cytometry and cell sorting. Efficiency is easily assessed with a flow cytometer (FACSCalibur, Becton-Dickinson) with cell sorting capability and using the destabilized form of the green fluorescent protein as a reporter, and simultaneously sort the transfected cells for further experimentation or transplantation. Thus, it is no longer necessary to rely on the generation of selected clones of insulinoma cells that stably express the transgene (problems with clonal variation). Transiently transfected cells separated from the non-transfected cells can be used. In addition, the flow cytometer also assesses cell viability (propidium iodide staining) and apoptosis (anti-activated caspase-3 antibody). In addition, the flow cytometer is also used for the sorting of rodent beta-cells, cell cycle analysis, mitochondrial membrane potential, production of oxygen free radicals and immunofluorescence studies (insulin, glucagon, Bcl-2).

EXAMPLE 2

Capsules with 4-[(4-methyl-1-piperazin-1-ylmethyl)-N-[4-methyl-3-[[4-(3-pyridinyl)-2-pyrimidinyl]amino]phenyl]benzamide methanesulfonate, Beta Crystal Form Capsules containing 119.5 mg of Salt I corresponding to 100 mg of Compound I (free base) as active moiety are prepared in the following composition:

| Composition: | Salt I | 119.5 mg |
|---|---|---|
| | Avicel | 200 mg |
| | PVPPXL | 15 mg |
| | Aerosil | 2 mg |
| | Magnesium stearate | 1.5 mg |
| | | 338.0 mg |

The capsules are prepared by mixing the components and filling the mixture into hard gelatin capsules, size 1.

EXAMPLE 3

Studies on the Mechanisms Underlying Compound I-Induced Protection Against Beta-Cell Death and Diabetes In Vivo Background: Compound I is known to inhibit c-Abl, an ubiquitously expressed protein tyrosine kinase with the approximate molecular weight of 145 kDa Under physiological conditions, c-Abl has been shown to participate in the control of cytoskeletal functions, such as migration and cell structure, and cell cycle progression. However, when cells are exposed to different forms of stress, c-Abl becomes highly activated, which leads to cell cycle arrest and apoptosis.

Recently obtained results: C-Abl is expressed in bTC-6 cells and in isolated rat islets, and inhibition of c-Abl activity, using the pharmacological agent Compound I, resulted in protection against beta-cell death induced by streptozotocin, proinflammatory cytokines or by nitric oxide donors. Compound I, e.g. Salt I is a selective inhibitor used clinically for the treatment of CML. In addition to c-Abl, Compound I is known to inhibit ABL oncogenes, c-KIT, the PDGFbeta receptor and the c-Abl homologue ARG. Thus it is necessary to shown that the Salt I effects are mediated specifically via inhibition of c-Abl. bTC-6 cells were therefore treated with either scrambled siRNA or siRNA specific for c-Abl. The siRNA is introduced into the cells using the Lipofectamine reagent. The cells are then followed for 1 or 3 days, after which total RNA is isolated. cDNA is synthesized from the RNA and used for PCR-amplification using primers specific for c-Abl (35 cycles) and b-actin, i.e. beta-actin (20 cycles). PCR products are separated on an agarose gel and visualized by ethidium bromide staining. No c-Abl band can be observed in cells 24 h after siRNA treatment (not shown). At 72 h, however, a c-Abl band appears. These results suggest that siRNA directed against c-Abl mediates knock-out of the messenger via the RNAi mechanism and that the effect is only transient in the rapidly proliferating bTC-6 cells (data not shown). Having established that c-Abl mRNA levels can be decreased with the RNAi technique, we next investigated whether bTC-6 cells deficient in c-Abl mRNA responded to the combination of IL-1β, IFN-γ and TFN-α with increased cell death. Contrary to the situation observed in primary islet cells, bTC-6 cells die in response to cytokines preferentially by apoptosis. Moreover, cytokine-induced bTC-6 cell death is potently counteracted by c-Abl specific siRNA two and three days after treatment (FIG. 3). This indicates that a presumably slow turnover of the c-Abl protein results in a delay in the effect of the siRNA-treatment. But more importantly, the data suggest that SALT I-induced protection against an NO-donor and the combination of cytokines is mediated by inhibition of c-Abl Connection between c-Abl and different MAP kinases: It is searched for a connection between c-Abl and the different MAP kinases p38, JNK and ERK that might act as down steam effectors of c-Abl. For this purpose, rat islets are pre-incubated for 24 with 10 μM Compound I and then exposed to DETA/NO (2 mM) and the combination of IL-1β, IFN-γ and TNF-α for 20 minutes. Islets are then analyzed for phosphorylation of p38, JNK2 and ERK1/2 using phosphospecific antibodies and immunoblotting. Compound I, e.g. Salt I, treatment partially (25-45%) counteracts the DETA/NO-induced activation of p38, JNK and ERK, and augmented the cytokine-induced MAPK activation (Tables 5 and 6).

TABLE 5

Effects of Compound I, e.g. Salt I, on DETA/NO- and cytokine-induced p38, JNK and ERK activation. Isolated rat islets are pre-incubated for 24 hours with 10 μM Compound I and then exposed for 20 min to DETA/NO or the cytokines IL-1β (50 U/ml) and IFN-γ (1000 U/ml). ERK, JNK and p38 phosphorylation is determined by immunoblotting and expressed per total amounts of ERK, JNK and p38.

| Treatment | Phospho-p38 | Phospho-JNK | Phospho-ERK |
|---|---|---|---|
| Control | 100 ± 44 | 100 ± 60 | 100 ± 69 |
| Compound I | 109 ± 39 | 213 ± 93 | 174 ± 94 |
| DETA/NO | 654 ± 213 | 360 ± 47 | 708 ± 167 |
| DETA/NO + Compound I | 497 ± 208 | 207 ± 53** | 482 ± 162 |
| Cytokines | 956 ± 252 | 800 ± 233 | 958 ± 148 |
| Cytokines + Compound I | 1484 ± 321 | 1250 ± 210* | 1179 ± 64 |

Results are expressed as percent of control and are means for 4 separate observations.
** and * denote $p < 0.01$ and $p < 0.05$, respectively, when comparing vs corresponding group without Compound I using 2-way ANOVA and Student's t-test.

TABLE 6

Results from Table 5 are recalculated so that the effects of Compound I are expressed in percent of corresponding group without any Compound I addition.

| Treatment | Phospho-p38 | Phospho-JNK | Phospho-ERK |
|---|---|---|---|
| DETA/NO | 100 | 100 | 100 |
| DETA/NO + Compound I | 76 | 57 | 67 |
| Cytokines | 100 | 100 | 100 |
| Cytokines + Compound I | 155 | 156 | 123 |

These results support that cytokine-induced nitric oxide production activates JNK and p38 at least partially via the c-Abl pathway and that this leads to beta-cell death. On the other hand, the early rise in p38 and JNK activity that occurs in response to cytokines appears to be suppressed by c-Abl. In this situation, however, it is likely that this first peak in cytokine-induced p38 and JNK activity represents a physiological response that leads to altered gene expression and increased proliferation, and not apoptosis per se. For example, it has been suggested that cytokine-activation p38 and JNK participates in the subsequent expression of the iNOS gene. In such a context, the presently observed c-Abl-mediated suppression of p38 and JNK explains nicely the increased nitric oxide production observed in islets treated with cytokines and Compound I.

In view of these data, c-Abl acts a sensor of stress and external death signals and that c-Abl activation might lead to phosphorylation and activation of the JNK and p38 MAP kinases and finally beta-cell death.

Additional Experiments:

1. To study the expression of c-Abl in beta-cells. c-Abl mRNA expression can be, assessed by real time-PCR. Levels of islet c-Abl mRNA is compared to those of other tissues. Fluorescent probes specific for c-Abl is purchased from TIB MOLBIOL Syntheselabor (Berlin, Germany) and fluorescent signals is quantified against a c-Abl cDNA standard curve using the Lightcycler instrument. Number of c-Abl mRNA molecules is standardized to b-actin mRNA molecules. The c-Abl mRNA content of human islets is compared to that of liver, muscle, kidney, spleen, brain and lung. In parallel the expression of the c-Abl-similar tyrosine kinase ARG, which might act in a similar fashion to c-Abl is quantified. In this context, it is determined whether levels of c-Abl mRNA are affected by cytokines, oxidative stress and ER stress. Human islets are exposed to IL-1β (25 U/ml)+IFN-γ (1000 U/ml)+ TNF-α (1000 U/ml), 100 mM hydrogen peroxide or brefeldin A (10 □M) for three hours and then analyzed for c-Abl mRNA expression by real-time PCR.

2. To study whether c-Abl is phosphorylated in response to beta-cell stress. Stable bTC-6 cell lines that over express wild type c-Abl are generated by lipofecting the cells with a pcDNA3/c-Abl plasmid (obtained from the Ludwig Institute, Uppsala University), followed by selection for resistance to geneticin. The c-Abl-over expressing bTC-6 cells are then exposed to IL-1, brefeldin A and DETA/NO for 20, 60, 360 min to establish whether c-Abl is phosphorylated in response to cytokines, ER stress and nitric oxide. Cells are then homogenized in the presence of phosphatase inhibitors, and c-Abl is immunoprecipitated using the K-12 anti-Abl antibody (Santa Cruz). After PAGE and transfer to nylon filters, c-Abl bands are analyzed for tyrosine phosphorylation at amino acid 245 and total tyrosine phosphorylation with two phosphospecific c-Abl antibodies (Tyr245 and Thr735) available from Cell Signaling Technology and the phosphotyrosine antibody 4G10. c-Abl activity is increased when the amino acid residues Tyr245 and Thr735 are hyper-phosphorylated.

3. To study whether the subcellular localization of c-Abl is affected by beta-cell stress. bTC-6 cells over expressing c-Abl are grown on cover slips and then exposed to cytokines, brefeldin A and a nitric oxide donor for six hours. Following fixation, blocking and permeabilization, the cells are analyzed by confocal microscopy using Mitotracker green (Molecular Probes), which stains mitochondria green, and the K-12 c-Abl antibody (Santa Cruz), which is, with a rhodamine-conjugated secondary antibody, stain c-Abl red. If c-Abl is re-localized from ER to mitochondria, the staining pattern is changed from -separated red and green to only yellow.

4. To Identify down-stream targets of c-Abl. For this purpose, CbTC-6 cells that transiently over-express wild-type or a constitutively active form of c-Abl are generated. bTC-6 cells are lipofected (Lipofectamine+Lipofectamine plus) with the pcDNA3/c-Abl-vector and a GFP-expression vector. This results in 20% GFP-positive cells, which are to be enriched to more than 75% by FACS. Sorted cells are plated and cultured for 24 h, and then analyzed for phosphorylation of the candidate targets ERK, JNK, p38, IκB, p53 and AKT (downateam effector of PI3K). Twenty and 120 min before analysis, cells are stimulated with doxorubicin (nuclear activation of c-Abl) or DETA/NO (cytoplasmic activation of c-Abl) with or without Salt I, e.g. Compound I.

Phosphorylation (ser/thr) of the putative target proteins are analyzed by immunoblotting using commercially available phospho-specific antibodies (Cell Signal Technology). This reveals whether the candidate effectors are phosphorylated and activated in response to c-Abl activation. Levels of Bcl-2, Bcl-$X_L$ and Aph2 using traditional Western blot technique are analyzed. In some instances, immunoprecipitation of candidate proteins is sometimes necessary to increase sensitivity of the immunoblot analysis. For tyrosine-specific phosphorylation, candidate effectors are immunoprecipitated and analyzed by immunoblotting using the PY20 anti-phosphotyrosine antibody.

5. To study the interaction between c-Abl and Shb:

Experiments are initiated aiming at understanding the putative interaction between the c-Abl and the adaptor protein Shb. Shb is an SH2-domain containing protein with proline-rich motifs in its N-terminus, a central PTB (phosphotyrosine binding)-domain, several potential tyrosine phosphorylation sites and a C-terminal SH2 domain, and is known to serve a role in generating signaling complexes in response to tyrosine kinase activation. Interestingly, the apoptotic propensity of Shb-over-expressing beta-cells is increased Indeed, transgenic mouse expressing SHB under the control of the rat insulin promoter displayed elevated rates of apoptosis when islets were cultured in the absence of serum or in the presence of cytotoxic cytokines. In view of a recent report showing that the Shb family member Shd binds to and interacts with c-Abl, it is possible that c-Abl acts via interactions with Shb in beta-cells. To investigate this, cells transiently transfected to over-express c-Abl, Shb or a Shb-mutant are treated with pervanadate and then immunoprecipitated with an anti-Shb-antibody. Immunoblotting is then performed on the immunoprecipitates to analyze levels of c-Abl and Shb, and tyrosine phosphorylation of c-Abl co-precipitated Shb. Preliminary findings indicate that c-Abl co-precipitates with Shb, and vice versa, and that c-Abl overexpression results in increased Shb-phosphorylation (data not shown). These findings support the notion that Shb is a substrate for the c-Abl kinase.

To further understand the interaction between c-Abl and Shb, fusion protein pull-down experiments are performed. GST, GST-ShbSH2 and GST-ShbPTB/proline-rich-domain fusion proteins is allowed to interact with COS-cell-homogenates containing high levels of c-Abl. The reactions is performed with or without pervanadate stimulation, i.e. to see importance of c-Abl tyrosine phosphorylation, and phosphotyrosine addition, i.e. to see importance of SH2-domain interaction with phosphotyrosine residue. Pull-down products are analyzed for c-Abl and phospho-c-Abl by immunoblotting. These experiments indicate which domains of Shb that are necessary for binding to non-phosphorylated or phosphorylated c-Abl. The corresponding experiments using c-Abl fusion protein (c-Abl-SH2 and c-Abl-SH3) are performed to evaluate which domains that are critical for binding to Shb.

To establish whether the Shb-c-Abl interaction mediates the enhanced propensity of Shb-overexpressing islet cells to undergo apoptosis in response to different noxious stimuli, islets are isolated from Shb-transgenic mice and exposed them to cytokines, DETA/NO and streptozotocin with or without pretreatment with Compound I. Apoptosis and necrosis are quantified and data obtained from the transgenic mice is compared with those of control mice obtained in parallel. If enhanced levels of apoptosis and necrosis of the Shb-islets are normalized by Compound I, e.g. Salt I, it is possible that the Shb-c-Abl interaction may be an essential apoptosis regulating pathway.

Facilities: RNAi. Studies are initiated aiming at turning off gene expression in beta-cells using the RNAi technique. Small interfering RNA (siRNA) is purchased from Dharmacon Research at a cost of 300-600 US dollar per pair of RNA oligonucleotides. Using FITC-labeled siRNA, it is observed that siRNA is efficiently introduced into insulin producing cells using Lipofectamine or Lipofectamine 2000 (results not shown). Unfortunately, the effect of liposomally delivered siRNA is only transient. For production of recombinant adeno-associated (AAV) vectors, the AAV Helper-Free System (Stratagene) is used. This kit includes plasmids for production of beta-gal expressing AAV-vectors used for preliminary transfection efficiency studies. Work with viral vectors has gained approval from the Swedish Government Agency Arbetarskyddstyrelsen.

Real-time PCR Lightcycler instrument (Roche) is a real-time PCR cycler. The apparatus allows rapid and accurate quantification of mRNA molecules, and is therefore suitable for studies of gene expression.

Confocal microscopy and Electron microscopy techniques are provided.

The invention claimed is:

1. A method of treatment for the delay of progression of type I or type II diabetes, which comprises administering to a patient in a pre-stage or in an early stage of type I or type II diabetes an effective amount of 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof.

2. A method according to claim 1 wherein the diabetes is type I diabetes.

3. A method according to claim 1 wherein the diabetes is type II diabetes.

4. A method according to claim 1 wherein the 4-(4-methylpiperazin-1-ylmethyl)-N-[4-methyl-3-(4-pyridin-3-yl)pyrimidin-2-ylamino)phenyl]-benzamide is in the form of the monomethanesulfonate salt.

5. A method of treatment for the remission of type I or type II diabetes, which comprises administering to a patient suffering from type I or type II diabetes an effective amount of 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof.

6. A method according to claim 5 wherein the diabetes is type I diabetes.

7. A method according to claim 5 wherein the diabetes is type II diabetes.

8. A method according to claim 5 wherein the 4-(4-methylpiperazin-1-ylmethyl)-N-[4-methyl-3-(4-pyridin-3-yl)pyrimidin-2-ylamino)phenyl]-benzamide is in the form of the monomethanesulfonate salt.

9. A method of treatment to suppress and/or reverse type I or type II diabetes, which comprises administering to a patient suffering from type I or type II diabetes an effective amount of 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof.

10. A method according to claim 9 wherein the diabetes is type I diabetes.

11. A method according to claim 9 wherein the diabetes is type II diabetes.

12. A method according to claim 9 wherein the 4-(4-methylpiperazin-1-ylmethyl)-N-[4-methyl-3-(4-pyridin-3-yl)pyrimidin-2-ylamino)phenyl]-benzamide is in the form of the monomethanesulfonate salt.

* * * * *